United States Patent [19]

Hollister

[11] Patent Number: 5,277,311
[45] Date of Patent: * Jan. 11, 1994

[54] NEEDLE ASSEMBLY HOLDER WITH ROTATABLE SAFETY SHEATH MEMBER AND METHOD OF EFFECTING PROPER ALIGNMENT OF A CANNULA USING SUCH NEEDLE ASSEMBLY HOLDER

[75] Inventor: William H. Hollister, Nelson, N.H.

[73] Assignee: Smiths Industries Medical Systems, Inc., Keene, N.H.

[*] Notice: The portion of the term of this patent subsequent to Oct. 13, 2009 has been disclaimed.

[21] Appl. No.: 977,715

[22] Filed: Nov. 17, 1992

Related U.S. Application Data

[63] Continuation-in-part of Ser. No. 947,841, Sep. 21, 1992, which is a continuation of Ser. No. 811,298, Dec. 20, 1991, Pat. No. 5,154,285.

[51] Int. Cl.$^5$ .......................... A61M 5/32; A61M 5/00; B65D 83/10
[52] U.S. Cl. ..................................... 206/365; 604/192
[58] Field of Search ............... 206/365, 438; 604/198, 604/192

[56] References Cited

U.S. PATENT DOCUMENTS

| | | | |
|---|---|---|---|
| 4,927,019 | 5/1990 | Haber et al. | 206/365 |
| 4,944,397 | 7/1990 | Miller | 604/198 |
| 4,982,842 | 1/1991 | Hollister | 206/365 |
| 5,139,489 | 8/1992 | Hollister | 604/192 |
| 5,151,089 | 9/1992 | Kirk, III et al. | 604/192 |
| 5,154,285 | 10/1992 | Hollister | 206/365 |

FOREIGN PATENT DOCUMENTS 9001348 2/1990 PCT Int'l Appl. ................. 604/192

*Primary Examiner*—William I. Price
*Attorney, Agent, or Firm*—Pollock, Vande Sande & Priddy

[57] ABSTRACT

The needle assembly holder of the present invention has mounted about its receptacle end a rotatable safety sheath so that irrespective of how the tip of the cannula of the needle assembly is oriented with respect to the holder, the user can nonetheless obtain an unobstructed view of the tip of the cannula by rotating the safety sheath out of her line of sight. Friction drag is provided between the receptacle end of the needle assembly holder and the safety sheath so that the safety sheath would not freely rotate about the needle assembly holder absent a rotation force applied thereagainst.

32 Claims, 8 Drawing Sheets

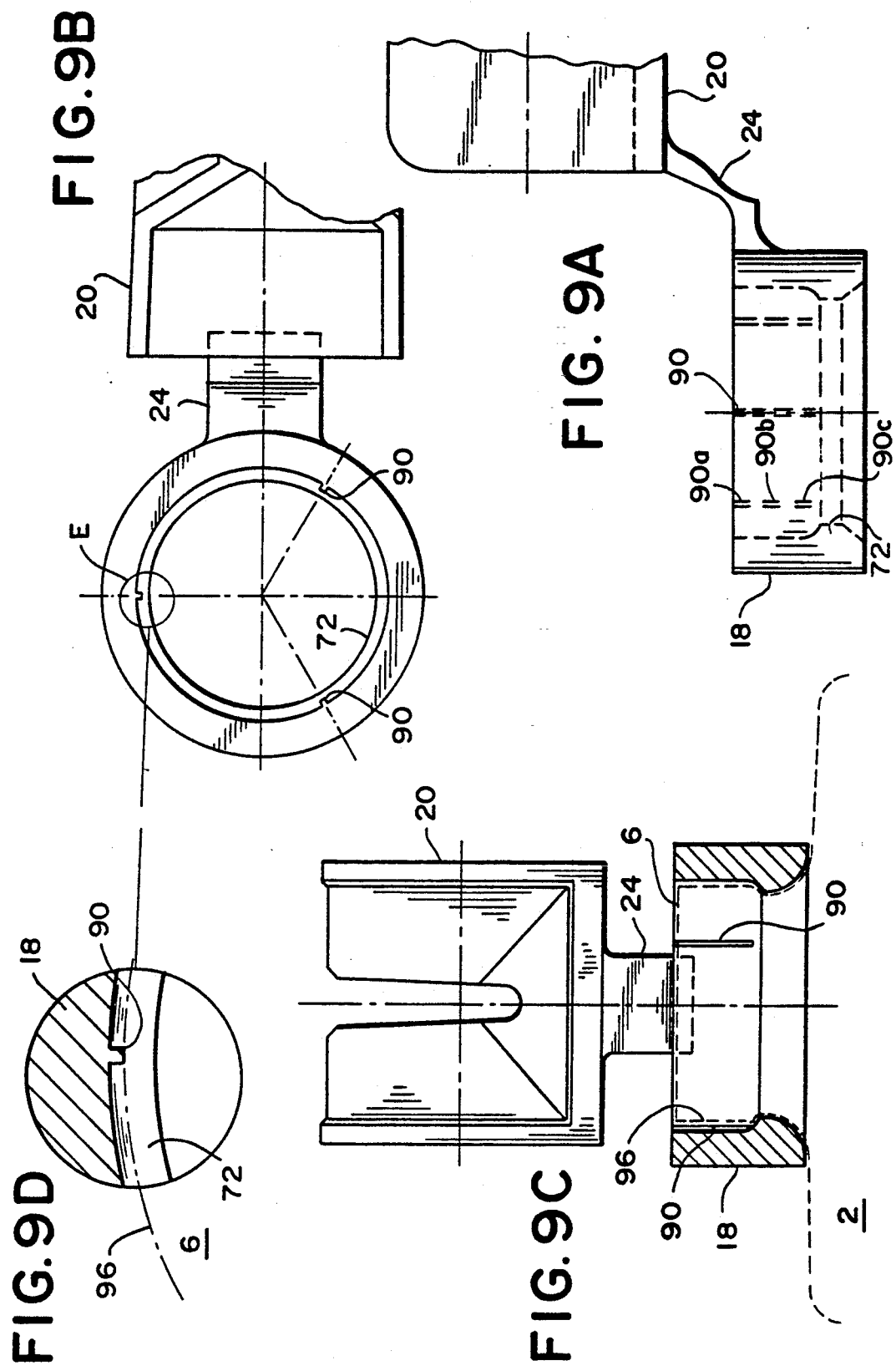

NEEDLE ASSEMBLY HOLDER WITH ROTATABLE SAFETY SHEATH MEMBER AND METHOD OF EFFECTING PROPER ALIGNMENT OF A CANNULA USING SUCH NEEDLE ASSEMBLY HOLDER

This is a continuation-in-part of U.S. patent application Ser. No. 947,841 filed Sept. 21, 1992, which in turn is a continuation of U.S. patent application Ser. No. 811,298, now U.S. Pat. No. 5,154,285, filed Dec. 20, 1991.

FIELD OF THE INVENTION

This invention relates to U.S. patent application Ser. No. 663,454, now U.S. Pat. No. 5,139,489 entitled "Needle Protection Device" filed March 4, 1991 by the same inventor and assigned to the same assignee as the instant invention. The disclosure of the '454 application is hereby incorporated to this application by reference. This invention is further related to U.S. patent application Ser. No. 561,459, entitled "Safety Needle Container", filed Aug. 1, 1990 by the same inventor and assigned to the same assignee as the instant invention. The disclosure of the '459 application is also hereby incorporated to this application by reference.

In particular, the present invention relates to a needle protection device to be used with a fluid holding tube which is adaptable to prevent a user, or a bystander, from being accidentally pricked by the sharp end of a contaminated needle.

BACKGROUND OF THE INVENTION

In the '454 application, a double-ended needle assembly holder, used in conjunction with an evacuated blood collection tube, is disclosed to have a housing that is pivotable to a position in substantial alignment with the longitudinal axis of the needle such that, once the housing is pivoted to the alignment position, the needle is retained therein so as to preclude the sharp end of the needle from being exposed.

The '454 safety device works well but for the fact that the user of the device, for example a phlebotomist or a nurse, is oftentimes blocked by the housing from having a clear view of the tip of the needle (cannula). To elaborate, ordinarily a phlebotomist, when obtaining fluid, as for example blood, from a patient, would position the cannula such that its bevel faces up. For this discussion, the bevel of a cannula is understood to be the sharp, butting end of the cannula. The reason that a phlebotomist wants to position the bevel of the cannula to face up is so that she can see the sharp point, rather than the round end, of the cannula so that the cannula can be more easily and accurately inserted into, for example the vein, of a patient. But since the needle assembly is threaded into the '454 safety device such that it may end up in any orientation, the safety housing attached to the '454 device would sometimes get in the way and prevent the phlebotomist from viewing the true angle of the cannula.

SUMMARY OF THE PRESENT INVENTION

To eliminate the sometimes disadvantageous aspect of the '454 device, the present invention safety device has attached to the extension of its tube holder a rotatable safety sheath member. Specifically, the holder extension has a circumferential protuberance, or boss, at its outer circumference. A safety housing, or sheath, whose base has a corresponding internal circumferential groove is mated with the holder extension such that the base is rotatable about the holder extension, via the interaction between the internal groove of the housing base and the external boss of the housing extension. With proper molding, friction between the internal groove of the base of the housing and the external boss of the holder extension can be such that the housing is not freely rotatable about the holder extension. In other words, in order to rotate the housing, a force has to be applied.

To further ensure that the housing is not freely rotatable about the holder extension, a variant of the present invention integrates at least one obstructive bump to the outer circumferential surface of the holder extension such that a frictional contact is effected between the housing and the holder. Yet another variant of the instant invention comprises the addition of, instead a bump, a number of fin-like extensions about the holder extension that coact with the base of the housing to frictionally prevent free rotation of the housing about the holder.

An alternative embodiment of the present invention includes the integration somewhere along the housing a crushable or collapsible section and the adaption of an elastomeric material at the cap section of the housing so that the tip of a contaminated needle can be securely sealed to provide yet an additional safety measure.

It is therefore an objective of the present invention to provide a safety needle assembly holder whose protective housing is rotatable away from the line of view of the user so that a cannula can be accurately inserted into a patient.

It is another objective of the present invention to provide a safety needle assembly holder whose rotatable protective housing is adapted to rotate only when a torque force is applied thereagainst.

BRIEF DESCRIPTION OF THE DRAWINGS

The above-mentioned objectives and advantages of the present invention will become more apparent and the invention itself will be best understood by reference to the following description of embodiments of the present invention taken in conjunction with the accompanying drawings, wherein:

FIG. 9A is a side view of the base portion, i.e. the collar, of the protective housing of the present invention that shows yet another variant of the present invention safety device;

FIG. 9B is a plan view of the FIG. 9A base portion;

FIG. 9C is a 90° rotated sectional view of the FIG. 9A base portion; and

FIG. 9D is an enlarged view of circled portion E of FIG. 9B.

DETAILED DESCRIPTION OF THE INVENTION

Figure 1:
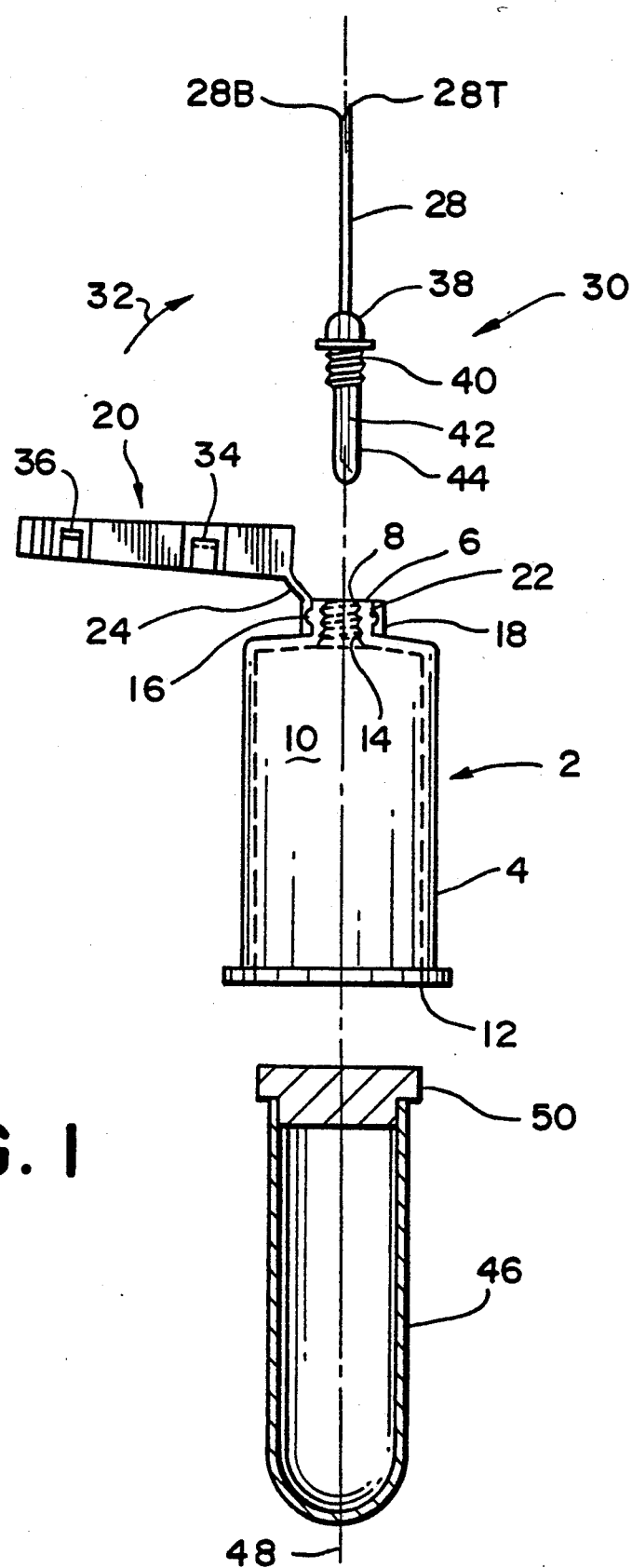
FIG. 1 is a side view of an embodiment of the present invention shown in alignment with a double-ended needle assembly and a fluid collection tube.

With reference to FIG. 1, the present invention safety device is shown to have a fluid container holder 2, otherwise known in the industry as a VACUTAINER holder, having a hollow main body section 4 and a receptacle end 6 integrally extending therefrom. An aperture extends from opening 8 of receptacle end 6 to cavity 10 of main body section 4. An opening 12 provides passage from the other end of holder 2 into cavity 10. The inner circumference of receptacle end 6 is threaded, as designated by 14.

For the present invention embodiment, formed around the outer circumference of receptacle end 6 is a circumferential protuberance, or boss, 16 about which a base or collar 18 of a safety sheath or housing 20 is fitted, via an internal circumferential groove 22 at base 18. Base 18 is substantially formed in the shape of a ring, a non-enclosed ring being shown in FIG. 4, and is hard-pressed onto receptacle end 6 for rotatably mating its internal groove 22 to external boss 16 of receptacle end 6. The respective dimensions of boss 16 and internal groove 22, and receptacle end 6 and base 18, are such that base 18 is held frictionally against receptacle end 6 so that the former is rotatable about the latter only by force. In other words, in order to rotate base 18 about receptacle end 6, a sufficient moment of torque is necessary. Putting it differently, once base 18 has been rotated to a certain orientation about receptacle end 6, it will stay in that orientation until additional torque force is exerted. Variants of the present invention in which additional measures are taken to ensure that housing 20 is not freely rotatable about receptacle end 6 are discussed below with reference to FIGS. 6, 7, 8 and 9.

Connected to base 18, via a flexible hinge 24, is housing 20. The construction of housing 20 has been given in detail in the above referenced '558 and '454 applications, as well as U.S. Pat. No. 4,982,842, the disclosure of which is incorporated by reference herein. Briefly, as shown in FIG. 1, housing 20 has an elongated slot 26 (see FIG. 3) through which a needle or cannula, such as 28 of the double-ended needle assembly 30, can pass when housing 20 is pivoted toward the longitudinal axis of cannula 28 via a force as indicated by directional arrow 32. Integrally formed within housing 20 are locking means such as, for example, hooking means (hooks) 34 and 36. It should be appreciated that there may be only one, or more than the two shown, hooking means integrated to housing 20. The hooking means each have a finger portion that biases against cannula 28 when housing 20 is pivoted to envelop the same, but which would then return to its original position once cannula 28 has passed the same to thereby permanently retain cannula 28 within housing 20. Thus, as discussed in detail in the herein incorporated by reference '842 patent, locking means 34 and 36 in essence prevent relative movement between cannula 28 and housing 20, once housing 20 has been pivoted to envelop the same.

The pivoting action of housing 20 is made possible by living hinge 24.

In operation, double-ended needle assembly 30 is connected to receptacle end 6 by turning its hub 38 so that it threadingly mates, via its threads 40, with the threaded aperture of receptacle end 6. Needle assembly 30 has, in addition to cannula 28, which is used to puncture, i.e. invasively contact a patient, an opposed cannula 42 surrounded by an elastomeric shroud 44. Once needle assembly 30 is mated with receptacle end 6, cannula 42 and shroud 44 are extended into cavity 10 of holder 2.

To allow a user a clear view of tip 28T so that cannula 28 can be more accurately inserted into the vein of a patient, for the present invention safety device, holder 2 can be reoriented such that bevel 28B is oriented to face up. And if housing 20 obstructs the view of the user from bevel 28B of cannula 28, it is rotated away by applying a torque force thereagainst so that base 18 rotates about receptacle end 6. Cannula 28 can therefore be clearly observed, as it is being inserted into the patient. Thereafter, a fluid container tube, such as 46, is inserted along longitudinal axis 48 through opening 12 into cavity 10 of holder 2. As tube 46 is pushed thereagainst, shroud 44 is pushed upwards so that the tip of cannula 42 would penetrate through elastomeric gasket 50 to effect fluid communication, via cannulas 28 and 42, between the patient and tube 46.

Once the necessary fluid, as for example blood, is withdrawn, tube 46 is removed from cavity 10. Thereafter, cannula 28 is removed from the patient. To ensure that the thus contaminated cannula 28 is not exposed and that no one is accidentally pricked thereby, by a single-handed operation, as for example pushing the end portion of housing against some immobile object, housing 20 is pivoted toward longitudinal axis 48 to envelop cannula 28. Either one, or both (or more if more than two hooks are integrated to housing 20), of hooks 34 and 36 would securely retain cannula 28 within housing 20. The thus used holder 2, along with the permanently retained needle assembly 30, may be disposed of in a safe manner as a single unit.

Figure 2:
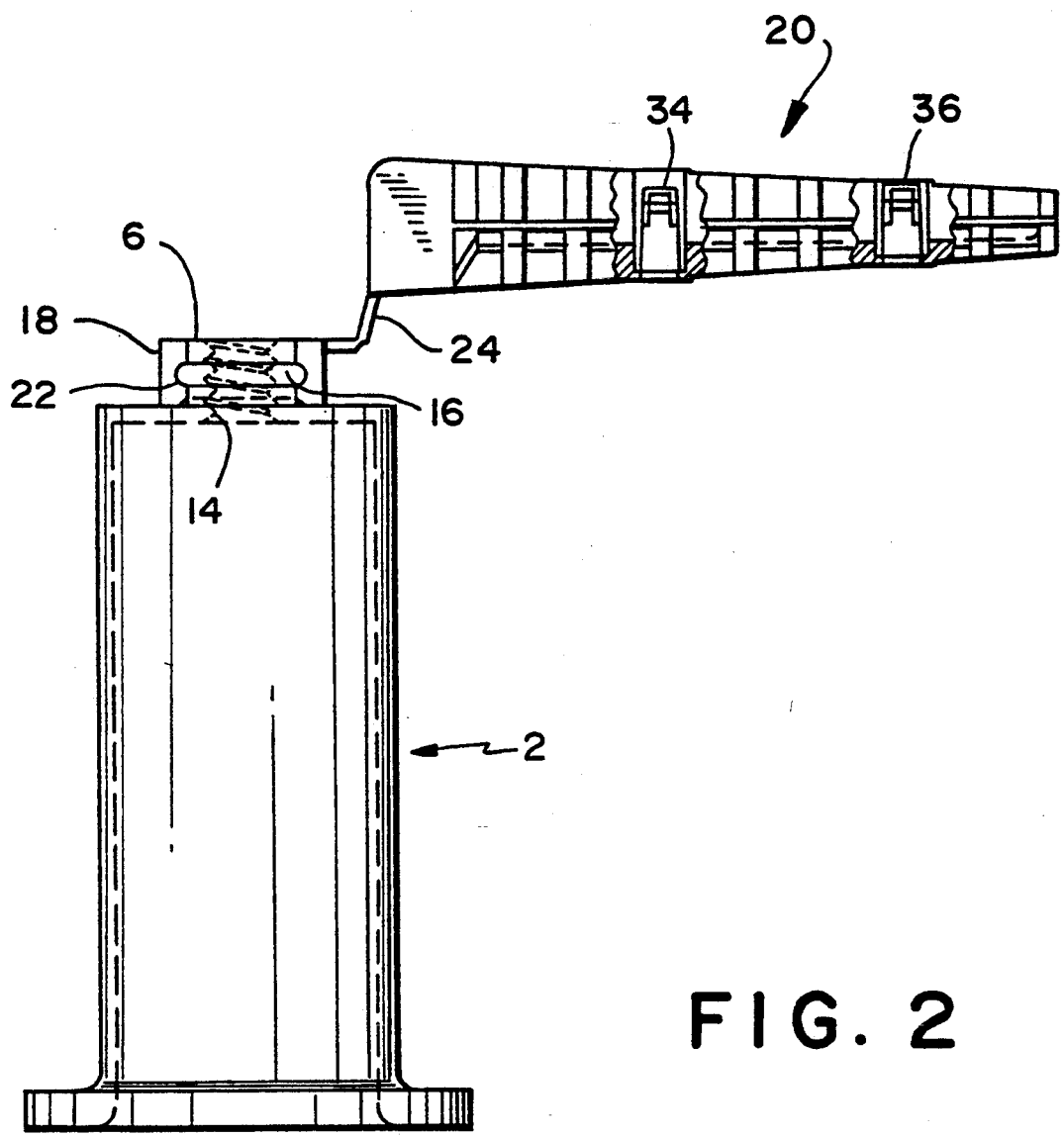
FIG. 2 is a semi-cutaway side view of the safety device of the present invention.
Figure 3:
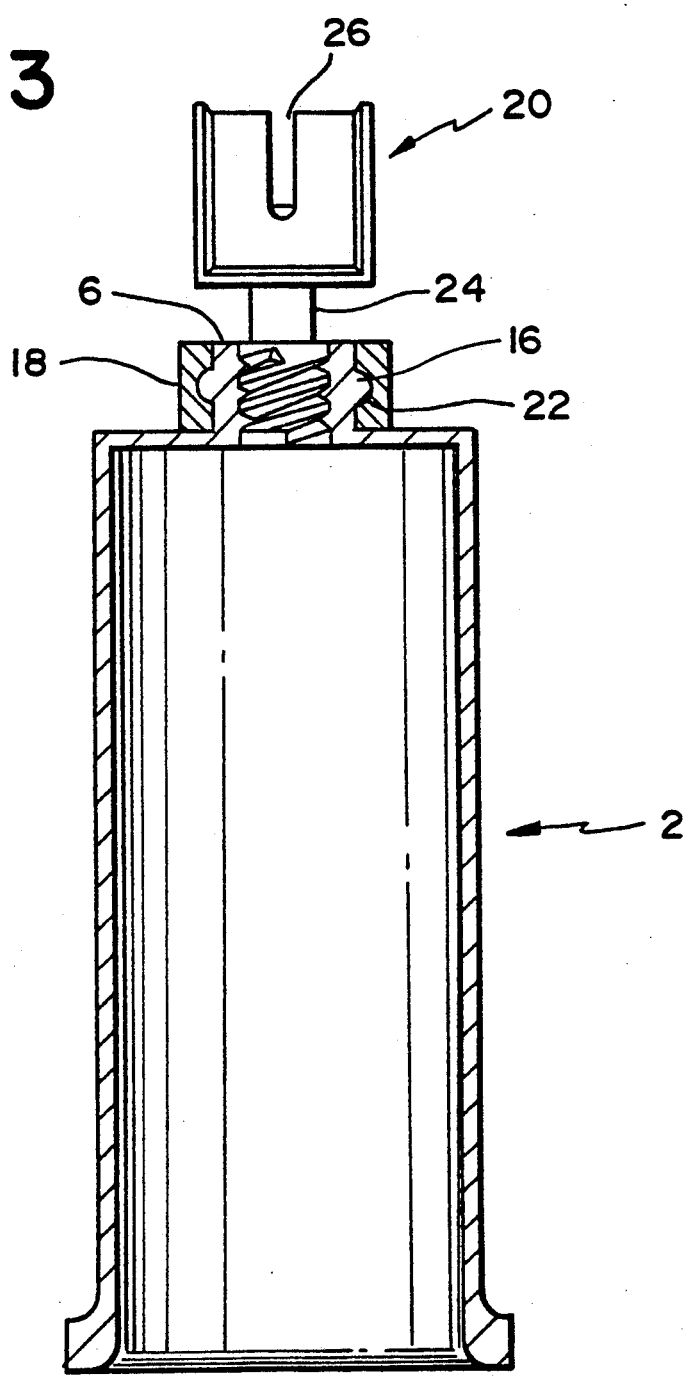
FIG. 3 is a cutaway front view of the safety device of the present invention.

FIGS. 2 and 3 show with greater detail and clarity tube holder 2 and the interaction thereof with housing 20 via the rotation of base 18 about receptacle end 6. The interaction between internal groove 22 of base 18 and circumferential boss 16 of receptacle end 6 is also more clearly illustrated in FIGS. 2 and 3.

Figure 4:
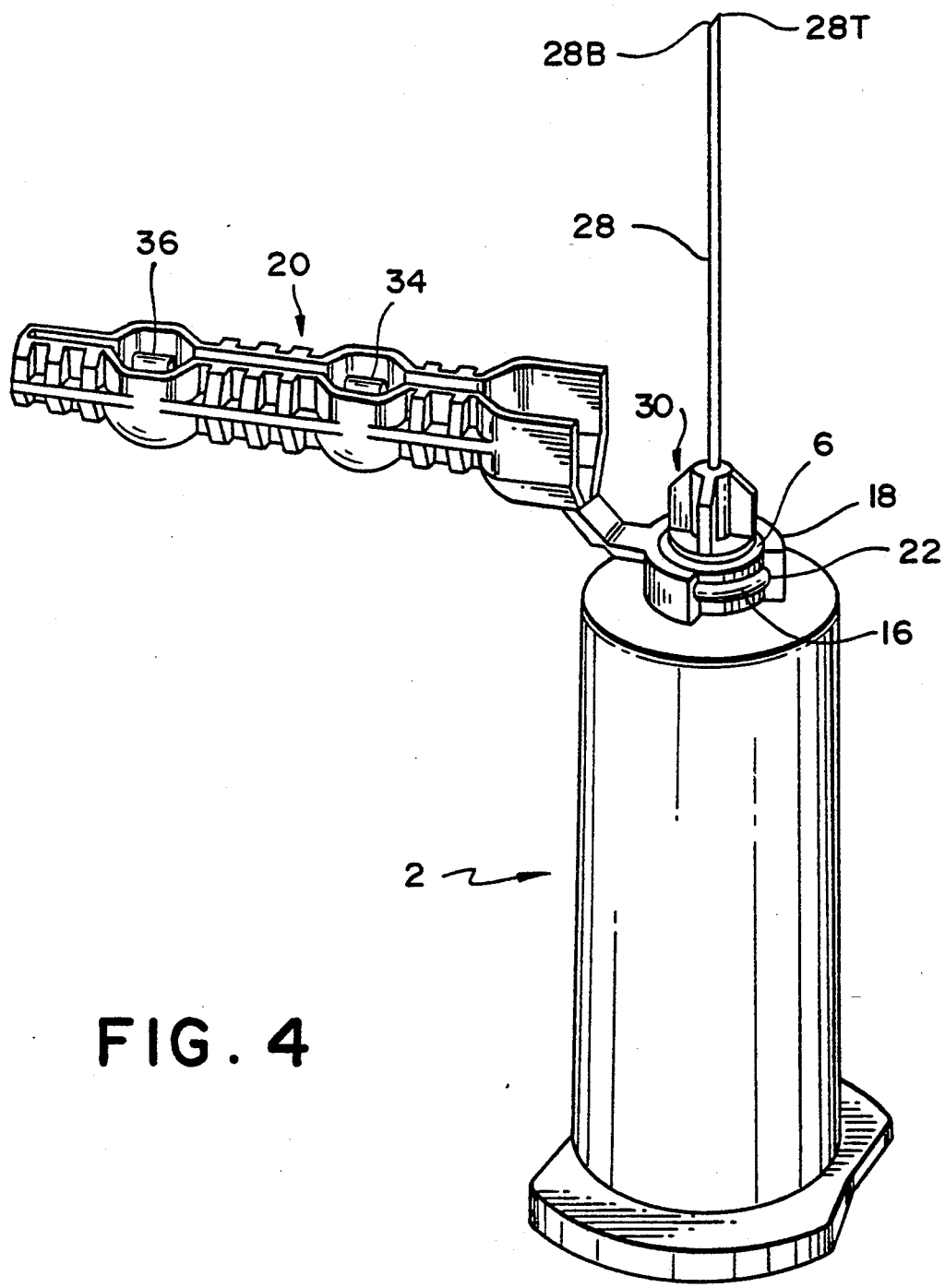
FIG. 4 is a perspective view of the safety device of the present invention having mated thereto a needle assembly.

FIG. 4 shows a perspective view of the present invention safety device having mated to its receptacle end 6 needle assembly 30. As shown, base 18 of housing 20 is not fully enclosed but rather is opened at one end so that it can be press fitted to receptacle end 6. As should readily be appreciated, base 18 can also be a fully enclosed ring or collar. In any event, base 18 can be formed with the requisite material (for example plastic) and dimension such that once it fittingly mates with receptacle end 6, it cannot be easily removed therefrom. Furthermore, the respective dimensions of base 18 and receptacle end 6, more specifically that of internal groove 22 and external boss 16, are such that the friction existing between the parts prevents base 18 of housing 20 from freely rotating about receptacle end 6. Thus, once housing 20 is moved to a given orientation, it stays in that orientation until it is further moved by a torque movement.

Figure 5:
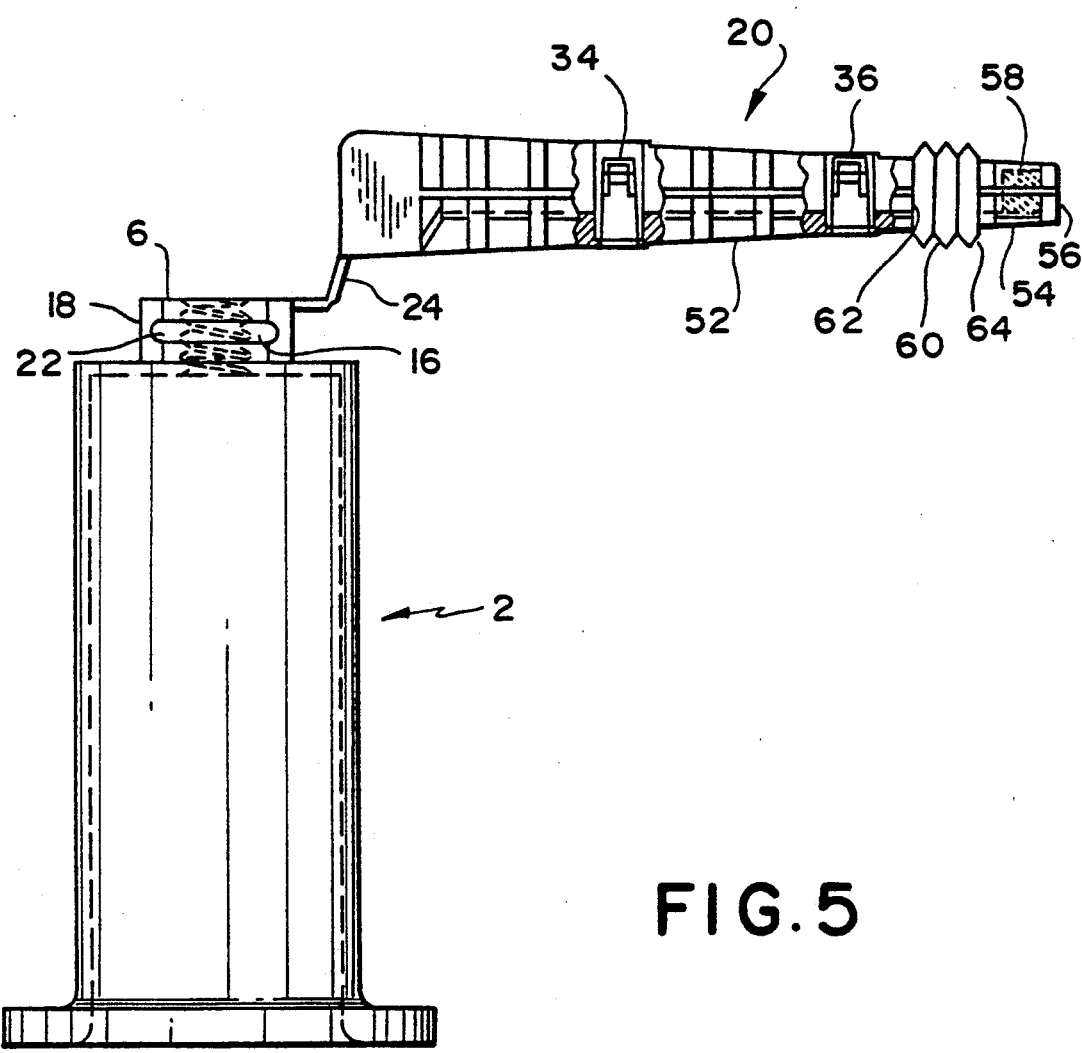
FIG. 5 is a semi-cutaway view of another embodiment of the present invention safety device.

FIG. 5 illustrates a second embodiment of the present invention. Elements that are the same as those of the previously discussed embodiment or perform the same functions are labelled the same. The FIG. 5 embodiment likewise has a base 18 which is rotatable about receptacle end 6 of holder 2, by means of the interaction between respective internal groove 22 and circumferential boss 16. For the FIG. 5 embodiment, however, housing 20 has a collapsible or crushable section 60 sandwiched between and integrally connecting a main body section 52 and a cap section 54. Adapted to cap section 54 is an elastomeric material 58 into which the tip of a contaminated cannula would penetrate—after housing 20 has been pivoted to envelop the cannula so that the same is securely retained by hooking means 34 and 36, and end 56 of housing 20 pushed longitudinally against an immobile object to effect a relative movement urging main body section 52 and cap section 54 toward each other to collapse crushable section 60. A more in depth discussion of the crushable section is given in the above incorporated by reference '459 application.

With reference to FIG. 6-9, variants of the present invention in which additional measures are taken to ensure that housing 20 does not rotate freely about receptacle end 6 absent a torque force applied thereagainst are illustrated.

Figure 6:
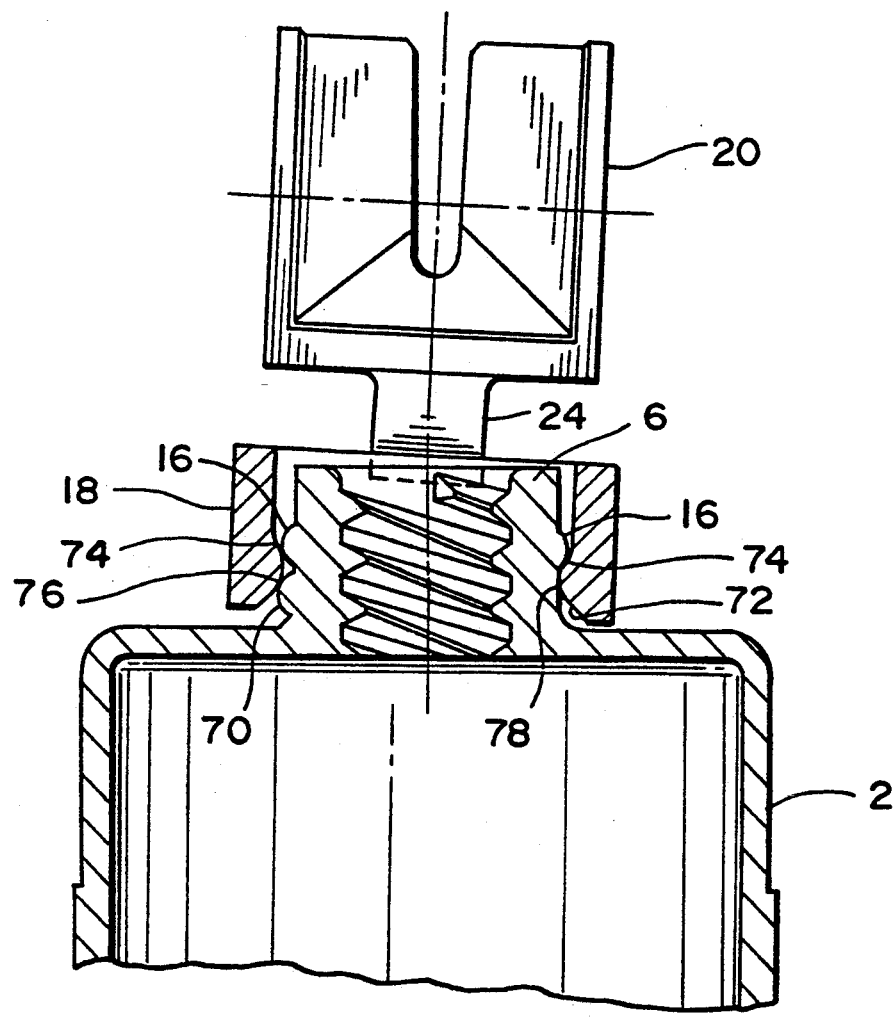
FIG. 6 is a cutaway view of a variant of the instant invention in which a bump is provided between the housing and the holder for enhancing the frictional contact therebetween.

As shown, for the FIG. 6 variant, an obstruction, for example an obstructive bump 70, is integrated to receptacle end 6 to effect friction contact between receptacle end 6 and base 18. For the FIG. 6 variant, it should be appreciated that base 18 of housing 20 may be fully enclosed to form a closed collar inasmuch as it has a somewhat beveled circumferential end portion 72 that allows base 18 to be forcibly fitted onto receptacle end 6 along the longitudinal axis of holder 2. The inner circumference of base 18, at contact point 74, coacts with the lower circumference of boss 16 to prevent base 18 from being separated from receptacle end 6. As shown, bump 70 coacts with an inner circumferential portion 76 of base 18 to thereby effect a more pronounced friction contact, or drag, between base 18 and receptacle end 6. In fact, as exaggeratedly shown in FIG. 6, the interaction between base 18 and bump 70 causes base 18 to tilt somewhat so that additional friction contact is created between base 18 and receptacle end 6 at a location, designated 78, that is opposite to the location of bump 70 at receptacle end 6. For the FIG. 6 variant of the present invention, therefore, given that bump 70 is formed at receptacle end 6, there no longer needs to be precise friction fitting between boss 16 and base 18. In fact, as shown in FIG. 6, the internal groove 22 shown in FIGS. 1-5 is no longer needed for base 18. Instead, a much easier manufactured portion 78 is formed at base 18 to ensure that base 18, once forced onto receptacle end 6, will not easily come off due to the interaction between boss 16 of receptacle end 6 and portion 72 of base 18.

Figure 7:
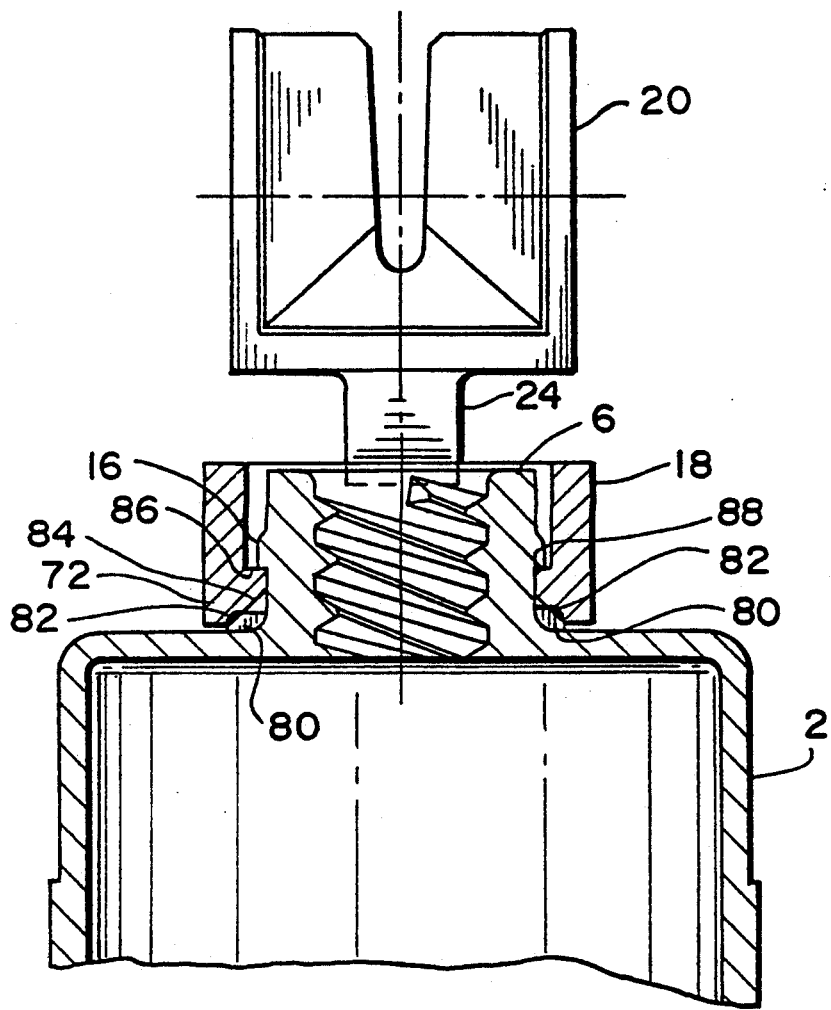
FIG. 7 is a cutaway view of yet another variant of the instant invention in which a number of fins are provided on the extension of the holder which coact with the base member of the housing to effect a frictional contact between the housing and the holder.

Yet another variant of the present invention for ensuring that sufficient friction contact is present between base 18 and receptacle end 6 so that housing 20 would only rotate if a torque force is applied thereagainst relative to holder 2 is shown in FIG. 7. There, instead of bump 70, a number of f in-like extensions 80 (fins) are provided around the lower portion of receptacle end 6 to coact with resistance against portion 72 of base 18 at junction 82. Accordingly, a plurality of friction contact points, corresponding to the number of fins 80 formed about receptacle end 6, are present to therefore maintain base 18, and housing 20, at a given rotational position, relative to holder 2, once a torque force against housing 20 is removed. And since there are now a plurality of fins 80 evenly spaced about receptacle end 6, base 18 is evenly aligned with receptacle end 6 and the rotation torque required to rotate housing 20 is more consistently applied thereagainst. Of course, it should be appreciated that only one fin 80, instead of bump 70, can also be used.

For the FIG. 7 variant of the present invention, portion 72 of base 18 is molded to have a beveled inner circumference 84, the lower portion of which coacts with fins 80, to provide for an easier mating of base 18 to receptacle end 6. Portion 72 further has at its upper end a circumferential ledge 86, which fittingly coacts with a corresponding circumferential surface 88 of boss 16. The interaction between surfaces 88 and 86 ensures that, once base 18 is inserted to receptacle end 6, it cannot be removed.

Figure 8:
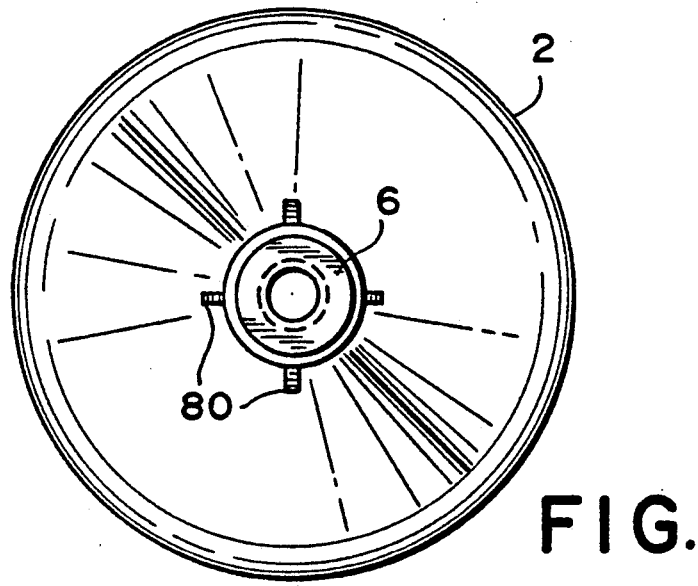
FIG. 8 is a plan view of the variant holder of the present invention shown in FIG. 7.

FIG. 8 is a plan view of holder 2, sans housing 20 and base 18, that shows that the FIG. 7 variant of the present invention has exemplar four fins 80 located 90° apart. Of course, instead of four fins 80 evenly spaced 90° apart about receptacle end 6, other configurations of evenly spaced fins 80, such as three fins 80 spaced 120° apart, would also provide the required frictional drag between base 18 and receptacle end 6.

With reference to FIGS. 9A-9D, yet another variant of the present invention is disclosed. As shown, base or collar 18 has integrated to its inner circumference a plurality of f in-like extensions 90 which, as more clearly shown in FIG. 9C, coact with the outer circumference 96 of receptacle end 6 of holder 2 (shown in dotted outline form to illustrate more clearly the fin-like extensions 90). For the variant shown in FIGS. 9A-9D, three fin-like extensions 90, evenly spaced at 120° about collar 18, are shown. It should be appreciated that, instead of three, some other multiples of fin-like extensions 90, for example four evenly spaced at 90°, may also be used. Thus, so long as there are a number of evenly spaced finlike extensions 90 in the inner circumference of collar 18 to coact with outer circumference 96 of receptacle end 6, a consistent drag is provided between inner circumference 90 of collar 18 and outer circumference 96 of receptacle end 6 when a torque force is applied against housing 20 to rotate the same relative to holder 2.

With specific reference to FIG. 9A, it should be appreciated that fin-like extension 90, instead of extending continuously from the mouth of collar 18 to section 72 thereof, can actually be comprised of a number of disjointed sections 90a to 90c, for example, each coacting with outer circumference 96 of receptacle end 6 to provide friction contacts between receptacle end and base 18, to thereby effect a consistent friction drag.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

I claim:

1. A method of effecting proper alignment of a first end of a needle assembly for insertion to a patient, said needle assembly mated to a receptacle end of a holder having a hollow main section into which at least a portion of a second end of said needle assembly extends, said method comprising the steps of:
- coupling to said holder housing means rotatable about said holder and pivotable to a position in substantial alignment along the longitudinal axis of said needle assembly for enveloping said first end of said needle assembly;
- rotating said housing means about said holder away from the line of sight of a user so that said user has an unobstructed view of the tip of said first end of said needle assembly.

2. The method of claim 1, wherein said coupling step further comprising the steps of:
- forming on the outer circumference of said receptacle end of said holder an annular boss;
- forming an internal circumferential groove at a base portion of said housing means;
- mating said base portion of said housing means to said receptacle end of said holder by rotatably fitting said circumferential groove about said boss so that said housing means is rotatable about said holder.

3. The method of claim 1, further comprising the step of:
- integrating holding means with said housing means to prevent relative movement between said housing means and said first end of said needle assembly once said housing means is pivoted to said alignment position to substantially envelop said first end of said needle assembly.

4. The method of claim 1, further comprising the steps of:
- adapting sealing means to a cap portion of said housing means for sealingly securing the tip of said first end of said needle assembly after said housing has been pivoted to said alignment position and said cap portion urged toward said holder.

5. The method of claim 4, further comprising the step of:
- interposing a collapsible section between said cap portion and a main portion of said housing means, said collapsible section collapses to thereby cause the tip of said first end of said needle assembly to be sealingly secured by said sealing means when said cap and main portions are relatively urged toward each other.

6. A safety device to be used with a needle assembly having a first and second end, comprising:
- a holder having a hollow main body section and a receptacle end extending therefrom, said holder further having an open end through which at least a portion of a container is insertable into said main body section, said receptacle end of said holder to be mated with said needle assembly such that at least a portion of said second end extends into said main body section;
- housing means rotatably coupled about said holder, said housing means having an elongated body portion pivotable to a position in substantial alignment along the longitudinal axis of said needle assembly to envelop said first end of said needle assembly, said body portion being rotatable about said needle assembly.

7. The safety device of claim 6, wherein said housing means has a base portion rotatably coupled about said receptacle end of said holder; and
- wherein said receptacle end has at its outer circumference an annular boss about at least a portion of which an internal circumferential groove of said base portion is rotatably mated to.

8. The safety device of claim 6, wherein said body portion of said housing means comprises a longitudinal sheath having an elongated slot through which said first end of said needle assembly passes when said sheath is pivoted to said alignment position.

9. The safety device of claim 7, wherein said body portion is integrally connected to said base portion by a flexible hinge means.

10. The safety device of claim 6, wherein said needle assembly comprises a hub; and
- wherein said receptacle end of said holder is internally threaded for threadedly mating with said hub of said needle assembly.

11. The safety device of claim 6, wherein said body portion of said housing means includes at least a cap portion and a main portion, further comprising:
- means adapted to said cap portion to substantially sealingly secure the tip of said first end of said needle assembly after said body portion has been pivoted to said alignment position and said cap portion urged toward said main portion.

12. The safety device of claim 11, further comprising:
- a collapsible section interposed between and integrally connecting said cap and main portions, said collapsible section collapsing to cause said sealing means to sealingly secure the tip of said first end of said needle assembly when said cap and main portions are relatively urged toward each other after said body portion has been pivoted to said alignment position.

13. A safety device for a double-ended needle assembly having opposed cannula portions, comprising:
- a holder having a hollow main body section and a receptacle end extending therefrom, said holder further having an open end through which at least a portion of a container is insertable into said main body section, said receptacle end of said holder being matable with said needle assembly such that at least a portion of one of said opposed cannula portions of said needle assembly extends into said main body section;
- housing means flexibly connected to and rotatable about at least a portion of said receptacle end of said holder, said housing means rotatable about said needle assembly and pivotable toward a position in substantial alignment along the longitudinal axis of said needle assembly for enveloping the other of said opposed cannula portions.

14. The safety device of claim 13, wherein said receptacle end has at its outer circumference a circumferential boss about at least a portion of which an internal circumferential groove of a base section of said housing means is rotatably mated to.

15. The safety device of claim 13, wherein said housing means comprises a longitudinal sheath having an elongated slot through which said other of said opposed cannula portions passes when said sheath is pivoted to said position.

16. The safety device of claim 13, wherein said housing means comprises a body section, and wherein said body section is integrally connected to said base section via a flexible hinge means.

17. The safety device of claim 13, wherein said body portion of said housing means includes at least a cap section and a main section, further comprising:

a collapsible section integrally interposed between and connecting said cap and main sections; and means adapted to said cap section of said housing means to substantially sealingly secure the tip of said other of said opposed cannula portions after said housing means has been pivoted to said substantial alignment position and said cap and main sections relatively urged toward each other to compress said collapsible section.

18. The method of claim 1, further comprising the steps of:

rotatably mating a base portion of said housing means to said receptacle end of said holder;

effecting friction contact between said receptacle end and said base portion such that said housing means is rotatable about said holder only when a torque force is applied thereagainst relative to said holder.

19. The method of claim 18, wherein said effecting step comprises the step of:

forming at least one obstruction means at the outer circumference of said receptacle end of said holder to effect said friction contact between said receptacle end and said base portion.

20. The method of claim 18, wherein said effecting step comprises the step of:

forming at least one obstruction means proximate to the base of the outer circumferential surface of said receptacle end of said holder to effect said friction contact between said receptacle end and said base portion.

21. The method of claim 18, wherein said effecting step comprises the step of:

forming at least one obstruction means at the inner circumference of said base portion for effecting said friction contact between said base portion and said receptacle end.

22. The method of claim 20, wherein said forming step comprises the step of:

forming at least one pair of fin-like extensions proximate to the base of the outer circumference of said receptacle end of said holder to effect said friction contact between said base portion and said receptacle end.

23. The safety device of claim 6, wherein said housing means comprises a base portion rotatably coupled about said receptacle end of said holder;

said safety device further comprising:

means for effecting friction contact between said receptacle end and said base portion such that said housing means is rotatable about said holder only when a torque force is applied thereagainst relative to said holder.

24. The safety device of claim 23, wherein said friction contact means comprises at least one bump integrated to the outer circumference of said receptacle end of said holder.

25. The safety device of claim 23, wherein said friction contact means comprises at least one fin-like extension integrated to the outer circumference of said receptacle end of said holder.

26. The safety device of claim 23, wherein said friction contact means comprises at least one pair of fin-like extensions integrated to the outer circumference of said receptacle end of said holder.

27. The safety device of claim 23, wherein said friction contact means comprises at least one fin-like extension formed at the inner circumference of said base portion.

28. The safety device of claim 13, wherein said housing means comprises a base portion rotatably coupled to said receptacle end of said holder;

said safety device further comprising:

means for effecting friction contact between said receptacle end and said base portion such that said housing means is rotatable about said holder only when a torque force is applied thereagainst relative to said holder.

29. The safety device of claim 28, wherein said friction contact means comprises at least one bump integrated to the outer circumference of said receptacle end of said holder.

30. The safety device of claim 28, wherein said friction contact means comprises at least one fin-like extension integrated to the outer circumference of said receptacle end of said holder.

31. The safety device of claim 28, wherein said friction contact means comprises at least a pair of fin-like extensions integrated to the outer circumference of said receptacle end of said holder.

32. The safety device of claim 28, wherein said friction contact means comprises at least one fin-like extension formed at the inner circumference of said base portion.

* * * * *